US012697106B2

(12) United States Patent
Mangat et al.

(10) Patent No.: US 12,697,106 B2
(45) Date of Patent: Aug. 4, 2026

(54) CORE NEEDLE BIOPSY DEVICE

(71) Applicants:NATIONAL UNIVERSITY HOSPITAL (SINGAPORE) PTE LTD, Singapore (SG); THE BIOFACTORY PTE LTD, Singapore (SG)

(72) Inventors: Kamarjit Singh Mangat, Birmingham (GB); Gabriel Hong Chun Tan, Singapore (SG); Ronald Craig Wight, Singapore (SG); Chun Siong Lee, Singapore (SG)

(73) Assignees: NATIONAL UNIVERSITY HOSPITAL (SINGAPORE) PTE LTD, Singapore (SG); IRNOVATE PTE LTD, Singapore (SG)

( * ) Notice: Subject to any disclaimer, the term of this patent is extended or adjusted under 35 U.S.C. 154(b) by 414 days.

(21) Appl. No.: 18/256,920

(22) PCT Filed: Dec. 10, 2021

(86) PCT No.: PCT/SG2021/050781
§ 371 (c)(1),
(2) Date: Jun. 10, 2023

(87) PCT Pub. No.: WO2022/124995
PCT Pub. Date: Jun. 16, 2022

(65) Prior Publication Data
US 2024/0023944 A1    Jan. 25, 2024

(30) Foreign Application Priority Data
Dec. 10, 2020    (SG) ............................ 10202012400T

(51) Int. Cl.
*A61B 10/02*        (2006.01)

(52) U.S. Cl.
CPC .. *A61B 10/0275* (2013.01); *A61B 2010/0208* (2013.01)

(58) Field of Classification Search
CPC . A61B 10/0233; A61B 10/0275; A61B 10/04; A61B 2010/0208; A61B 2010/045
See application file for complete search history.

(56) References Cited

U.S. PATENT DOCUMENTS 6,419,641 B1 *  7/2002  Mark ................. A61B 10/0275
                                                      600/564
8,882,681 B2 *  11/2014  Neoh ................. A61B 10/0275
                                                      600/566

(Continued)

FOREIGN PATENT DOCUMENTS

AU        728656 B2      1/2001
EP        1731104 A1     12/2006

(Continued)

*Primary Examiner* — Devin B Henson
(74) *Attorney, Agent, or Firm* — SOROKER AGMON NORDMAN

(57)            ABSTRACT

The present disclosure provides a biopsy device for performing soft tissue biopsy on any major organ through the venous system, and a method for using the biopsy device. The biopsy device of the present disclosure is a system that is sufficiently flexible such that the system can be guided manually and with existing tools i.e., fluoroscopy for visualisation and simple guidewires. Once in place, the biopsy device of the present disclosure can generate enough force and can transmit that force to the distal cutting end of the system to penetrate the organ and obtain a biopsy.

21 Claims, 10 Drawing Sheets

(56) References Cited

U.S. PATENT DOCUMENTS

| 9,125,637 | B2 * | 9/2015 | Callede | A61B 10/0233 |
|---|---|---|---|---|
| 12,318,076 | B2 * | 6/2025 | Nevo | A61B 10/0275 |
| 2008/0242925 | A1 | 10/2008 | Suda | |
| 2009/0247900 | A1 | 10/2009 | Zimmer | |
| 2013/0226030 | A1 * | 8/2013 | McGhie | A61B 10/0275 |
| | | | | 600/567 |
| 2014/0005478 | A1 * | 1/2014 | Kennedy, II | A61B 1/00066 |
| | | | | 600/114 |
| 2014/0171826 | A1 * | 6/2014 | Lampropoulos | A61B 10/0275 |
| | | | | 600/562 |

FOREIGN PATENT DOCUMENTS

| JP | 2003525064 | A | 8/2003 |
|---|---|---|---|
| JP | 2015205206 | A | 11/2015 |
| JP | 2019523665 | A | 8/2019 |
| WO | 2005096778 | A2 | 10/2005 |
| WO | 2007009901 | A1 | 1/2007 |
| WO | 2011018091 | A1 | 2/2011 |
| WO | 2014081812 | A1 | 5/2014 |
| WO | 2018127848 | A1 | 7/2018 |
| WO | 2018182937 | A2 | 10/2018 |

* cited by examiner

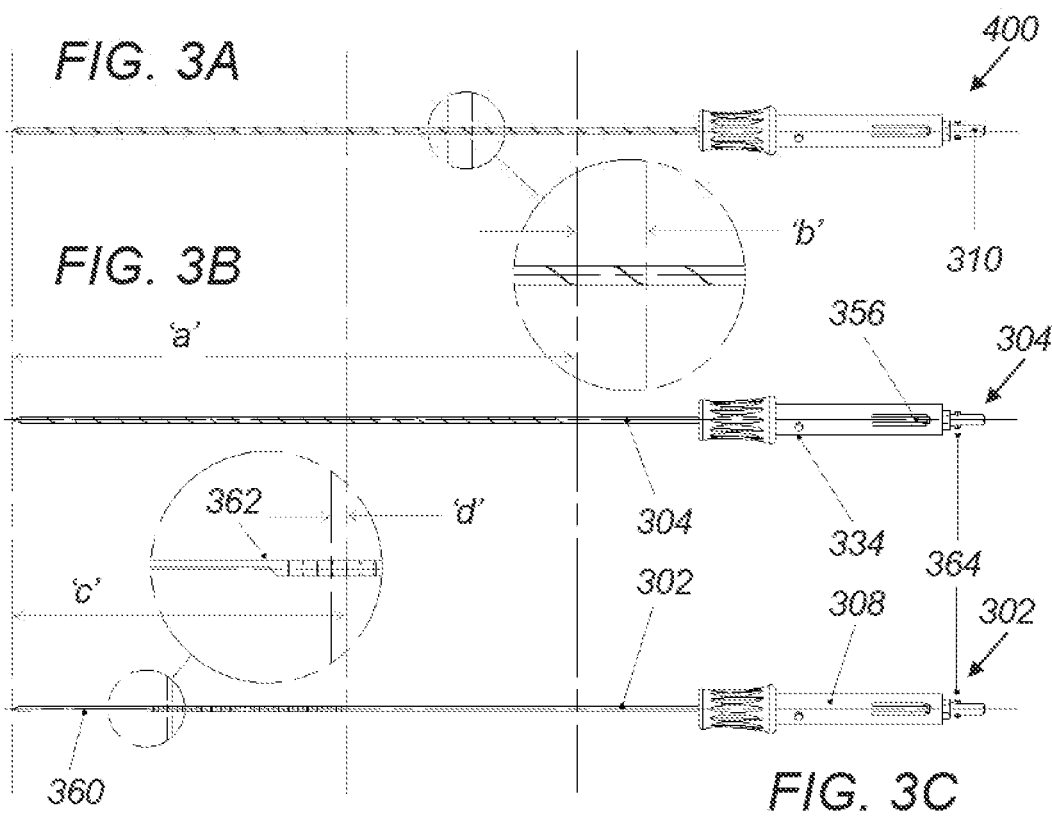
*FIG. 3A*
*FIG. 3B*
*FIG. 3C*
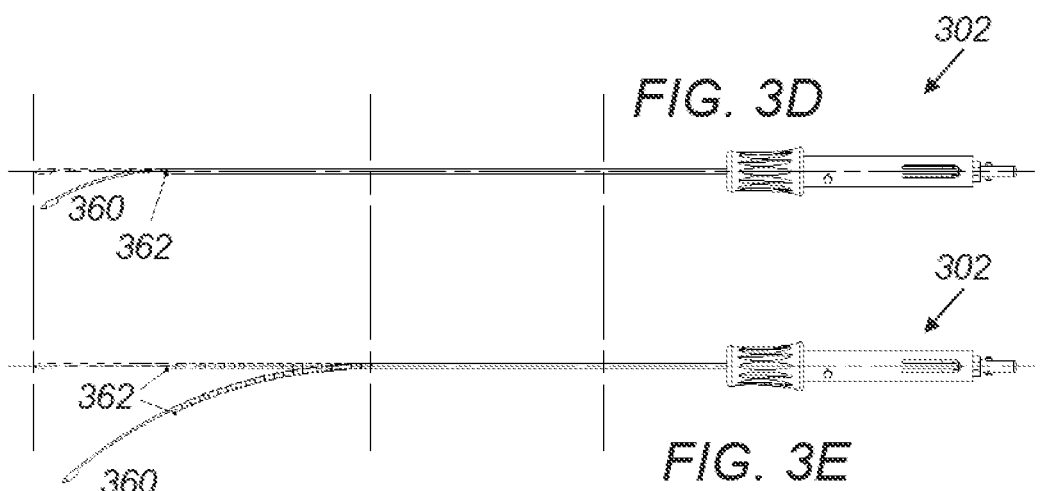
*FIG. 3D*
*FIG. 3E*

CORE NEEDLE BIOPSY DEVICE

TECHNICAL FIELD

The present disclosure relates to biopsy devices, and more particularly to a biopsy device for acquiring a biopsy sample of a target organ. In particular, the present disclosure relates to a biopsy device with a flexible surgical instrument that can be inserted at a peripheral vascular access site through a catheter for performing soft tissue biopsy.

BACKGROUND

Current methods for performing liver biopsies may include an inherent risk of severe complications, which may often result in patients opting to delay the biopsy procedure, thus delaying subsequent diagnosis and intervention of liver dysfunction. The methods may include open surgery, percutaneous liver biopsy (PLB), and trans-jugular liver biopsy (TJLB).

Open surgery liver biopsy is the direct removal of liver tissue during a laparoscopic, or surgical procedure. Open surgical liver biopsy in modern practice may be utilized when there is already a surgical procedure underway.

Percutaneous liver biopsy (PLB) may involve extracting a core sample of liver tissue using a biopsy needle inserted through the abdominal wall. In PLB, the liver capsule is punctured, and a high penetration depth is needed to reach the parenchyma. This procedure may often provide good biopsy samples, but the procedure is invasive, painful, and may carry a risk of significant complications, including a significant risk of death (1 in 250). If the first biopsy fails and additional biopsy samples are needed, additional needle punctures may be required, further increasing the risk of complications. Thus, PLB patients may be kept under observation for several hours after the procedure to ensure that there is no bleeding into the peritoneal cavity due to the puncturing of the liver capsule or vessels.

TJLB involves accessing the liver through the insertion of a stiff metal catheter into the right or left jugular vein and navigating the catheter through the right chamber of the heart and into the hepatic vein of the liver. A large bore needle directed down the catheter is used to core the liver tissue. Multiple samples are often needed for satisfactory analyses.

TJLB may avoid the risk of undetected bleeding into the peritoneum since any bleeding from the needle punctures as in PLB drains back into the hepatic vein. Since TJLB involves navigating a stiff metal catheter through major organs and blood vessels the procedures may result in significant complications such as haemorrhaging, arrhythmia, vessel perforation, pneumothorax, or death. Although TJLB may be considered to be safer than PLB, TJLB does incur new risks of complications related to its jugular access site.

Existing single-use, disposable mechanisms for obtaining percutaneous biopsy tissue samples fire a spring-loaded stylet at high speed into a target lesion followed immediately thereafter by the coring needle or cutting cannula to obtain a sample of the target lesion. The firing mechanism is configured such that the stylet and the coring needle are integral within the mechanism. This may suffice for percutaneous applications with the aid of ultrasound, but it embodies considerable risk for TJLB. If the firing mechanism were inadvertently loaded prior to insertion, there is an inherent risk of the mechanism firing prematurely whilst being inserted through the right brachiocephalic vein or the superior vena cava due to operator error or malfunction of the firing mechanism. Furthermore, there is a significant risk for patients if TJLB is performed multiple times to ensure that sufficient sample is retrieved for analysis.

Thus, there is a need for a transvenous biopsy device that can be introduced into the peripheral venous system of the arm into the patient's body via the basilic/cephalic veins, for example, and flexibly navigated through the venous system for performing a soft tissue biopsy on a target organ, such as the liver, so as to reduce the risk of major complications associated with PLB and TJLB procedures.

International Patent Publication 2019/103694A1 by the current applicant and published May 31, 2019, the disclosure of which is incorporated herein by reference describes a balloon-anchored biopsy device. However, although this was sufficient for most applications, there were some issues. As the distal end of the balloon catheter is anchored in the hepatic vein when the balloon is inflated, there would be insufficient force generated to penetrate the organ due to recoil.

It is desirable to provide an improved biopsy device given the current apparatus used for obtaining a core specimen from soft tissue.

SUMMARY

An aspect of an embodiment of the disclosure relates to a biopsy device for performing soft tissue biopsy on any major organ through the venous system. The biopsy device of the present disclosure is a system that is sufficiently flexible such that the system can be guided manually and with existing tools i.e., fluoroscopy for visualisation and simple guidewires. Once in place, the biopsy device of the present disclosure can generate enough force and can transmit that force to the distal cutting end of the system to penetrate the organ and obtain a biopsy. In addition, the biopsy device of the present disclosure allows part of the system to be withdrawn with a soft tissue sample for inspection and collection without complete withdrawal of the system. The withdrawn part of the system may subsequently be re-inserted with minimal risk for an additional sample if the previous sample was found to be insufficient.

According to embodiments of the present disclosure, there is provided a biopsy device for acquiring a biopsy sample of a target organ in a subject, the biopsy device comprising: a housing; and an elongated tube with a first proximal end and a first distal end, wherein the first distal end is positioned at a biopsy site of the target organ, and wherein the first proximal end comprises a first locking mechanism, said first locking mechanism is coupled to the housing.

According to some embodiments, the biopsy device may further comprise a biopsy needle with a second proximal end and a second distal end, the biopsy needle is positioned within the elongated tube for navigation to the biopsy site and is configured to exit the first distal end of the elongated tube for penetration into tissue of the target organ at the biopsy site, and to acquire a biopsy sample of the target organ at the biopsy site, and wherein the second proximal end of the biopsy needle comprises a second locking mechanism, said second locking mechanism is coupled to the housing. Optionally, the first locking mechanism comprises a swivel and a bayonet. Optionally, the first locking mechanism comprises opposing extensions configured to engage with the inside of an opening in the housing. Optionally, each of the opposing extensions comprise a shoulder configured to engage with the inside of the opening in the housing. Optionally, the first locking mechanism is freely rotatable around the elongated tube.

According to some embodiments, the biopsy needle comprises a coring needle and a stylet needle. The second locking mechanism may comprise a cartridge and a stylet lug. Optionally, the coring needle comprises one or more spiral cuts extending circumferentially around and longitudinally along the coring needle. Optionally, the one or more spiral cuts has a constant pitch. Alternatively, the one or more spiral cuts has a variable pitch.

According to some embodiments, the stylet needle comprises notches along its circumference longitudinally along the stylet needle. Optionally, the notches are diametrically opposed. Optionally, the notches are of a depth of not more than 30% of the stylet needle diameter. Optionally, the notches are rotated 90 degrees axially.

According to some embodiments, the housing further comprises an advancing mechanism, configured to advance the stylet needle for penetration into tissue of the target organ at the biopsy site; and a firing mechanism, configured to fire the coring needle for penetration into tissue of the target organ at the biopsy site, thereby obtaining the biopsy sample of the target organ at the biopsy site. Optionally, the advancing mechanism is actuated by rotation. Optionally, the firing mechanism is configured to fire the coring needle only when the stylet needle is fully advanced. Optionally, the stylet needle comprises an indentation at a third distal end of the stylet needle.

According to some embodiments, there is provided a method for acquiring a biopsy sample of a target organ in a subject using a biopsy device, the method including: providing a biopsy device, the biopsy device comprising: a housing; an elongated tube with a first proximal end and a first distal end, wherein the first distal end is positioned at a biopsy site of the target organ, and wherein the first proximal end comprises a first locking mechanism, said first locking mechanism is coupled to the housing; and a biopsy needle with a second proximal end and a second distal end, the biopsy needle is positioned within the elongated tube for navigation to the biopsy site and is configured to exit the first distal end of the elongated tube for penetration into tissue of the target organ at the biopsy site, and to acquire a biopsy sample of the target organ at the biopsy site, and wherein the second proximal end of the biopsy needle comprises a second locking mechanism, said second locking mechanism is coupled to the housing; percutaneously inserting the elongated tube into a first blood vessel of a limb of a subject; and navigating the first distal end of the elongated tube from the first blood vessel through a vascular system of the subject and into a second blood vessel of the target organ near the biopsy site.

According to some embodiments, the first locking mechanism may comprise opposing extensions configured to engage with the inside of an opening in the housing. Optionally, coupling the elongated tube to the housing with the first locking mechanism comprises: compressing the opposing extensions; and inserting the compressed opposing extensions into the opening in the housing. Optionally, the biopsy needle comprises a coring needle and a stylet needle.

According to some embodiments, the method may further comprise the steps of pushing the stylet needle into the target organ at the biopsy site until the stylet needle is fully advanced; and pushing the coring needle into the target organ at the biopsy site.

BRIEF DESCRIPTION OF THE DRAWINGS

In order for the present disclosure, to be better understood and for its practical applications to be appreciated, the following Figures are provided and referenced hereafter. It should be noted that the Figures are given as examples only and in no way limit the scope of the invention.

FIG. 3A schematically illustrates a needle assembly, in accordance with some embodiments of the present disclosure;

FIG. 3B schematically illustrates a coring needle of a needle assembly, in accordance with some embodiments of the present disclosure;

FIG. 3C schematically illustrates a stylet needle of a needle assembly, in accordance with some embodiments of the present disclosure;

FIG. 3D schematically illustrates the bending of an unnotched stylet needle, in accordance with some embodiments of the present disclosure;

FIG. 3E schematically illustrates the bending of a notched stylet needle, in accordance with some embodiments of the present disclosure;

Figure 1A:
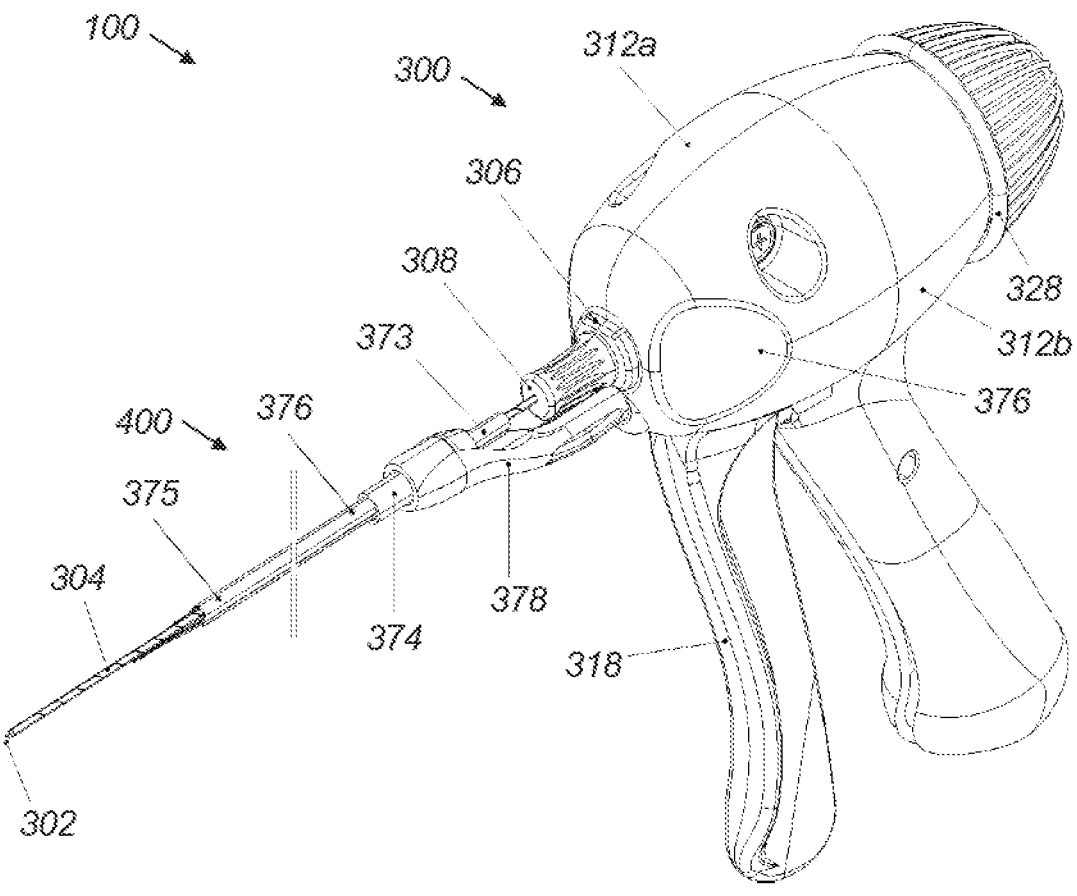
FIG. 1A schematically illustrates a biopsy device, in accordance with some embodiments of the present disclosure.

With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

Identical or duplicate or equivalent or similar structures, elements, or parts that appear in one or more drawings are generally labeled with the same reference numeral, optionally with an additional letter or letters to distinguish between similar entities or variants of entities, and may not be repeatedly labeled and/or described. References to previously presented elements are implied without necessarily further citing the drawing or description in which they appear.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

DETAILED DESCRIPTION

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

Embodiments of the present disclosure herein describe a core needle biopsy device for peripheral access (e.g., transcephalic access) that overcomes problems of insufficient force transfer from the handle to the cutting cannula and stylet at the biopsy site. The core needle biopsy device further includes safety mechanisms by preventing premature firing of the coring needle as well as providing separate locking mechanisms for the cannula and the biopsy needle. Finally, the present disclosure includes the coupling of a balloon-anchored catheter to the mechanism that advances a stylet needle and a coring needle of a biopsy needle to stabilize the balloon-anchored catheter and allow the advancement of the stylet needle without holding onto the balloon-anchored catheter.

Figure 1B:
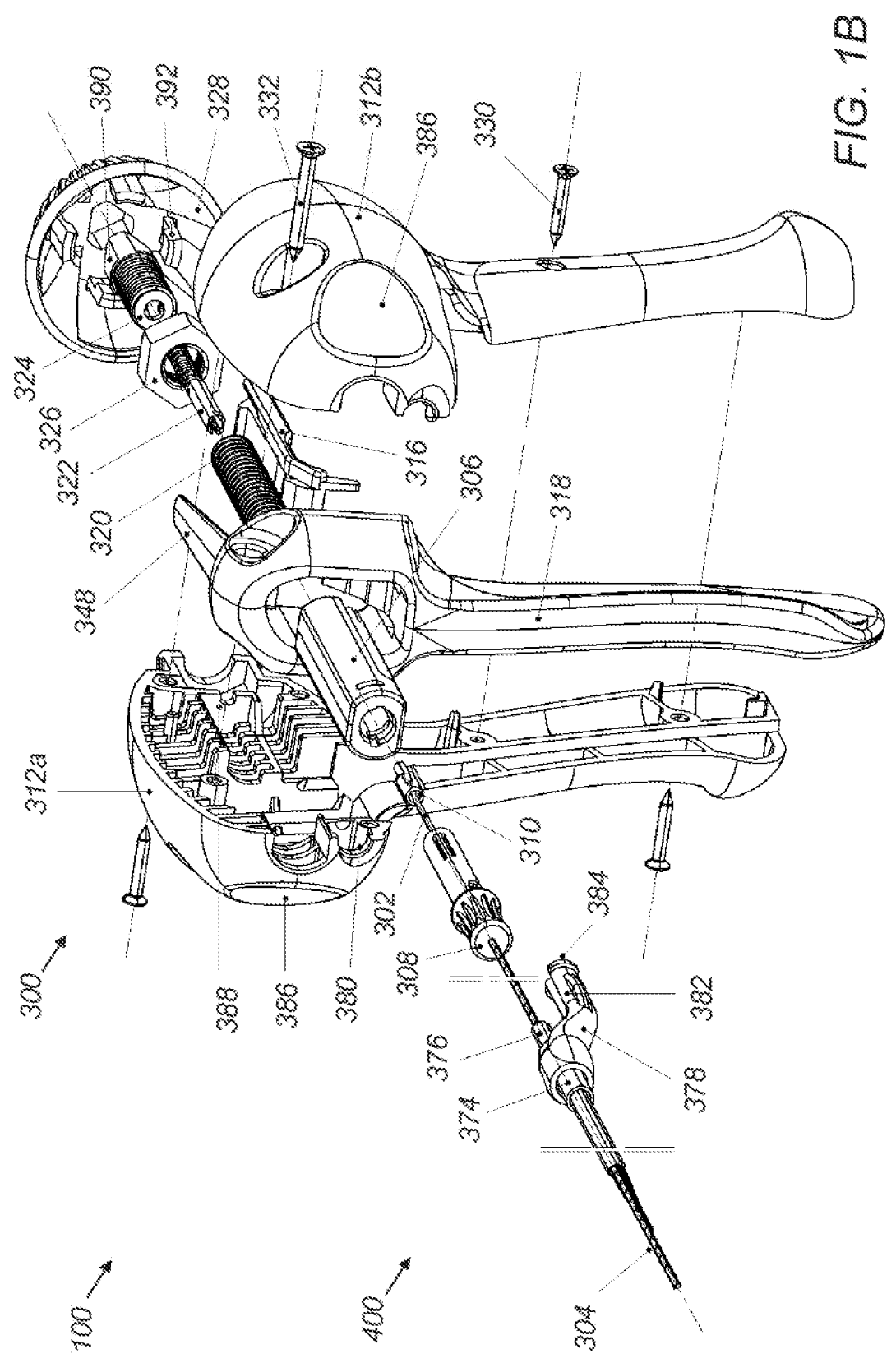
FIG. 1B schematically illustrates an exploded view of a biopsy device, in accordance with some embodiments of the present disclosure.

FIG. 1A schematically illustrates a biopsy device 100 while FIG. 1B schematically illustrates an exploded view of a biopsy device 100, in accordance with some embodiments of the present disclosure. Biopsy device 100 comprises a gun 300, a needle assembly 400 and an elongated tube 376. Biopsy device 100 is used to fire a biopsy needle 363 that has been inserted into a patient via an elongated tube 376. For the purpose of illustration, in the description, the elongated tube 376 may be described as a catheter 376, though it should be understood that other elongated tubes like cannulas can be used. Catheter 376 comprises a proximal end 373 and a distal end 375. Distal end 375 of catheter 376 is positioned at a biopsy site of a target organ. The target organ may be any organ, including the liver parenchyma.

Figures 2A, 2B:
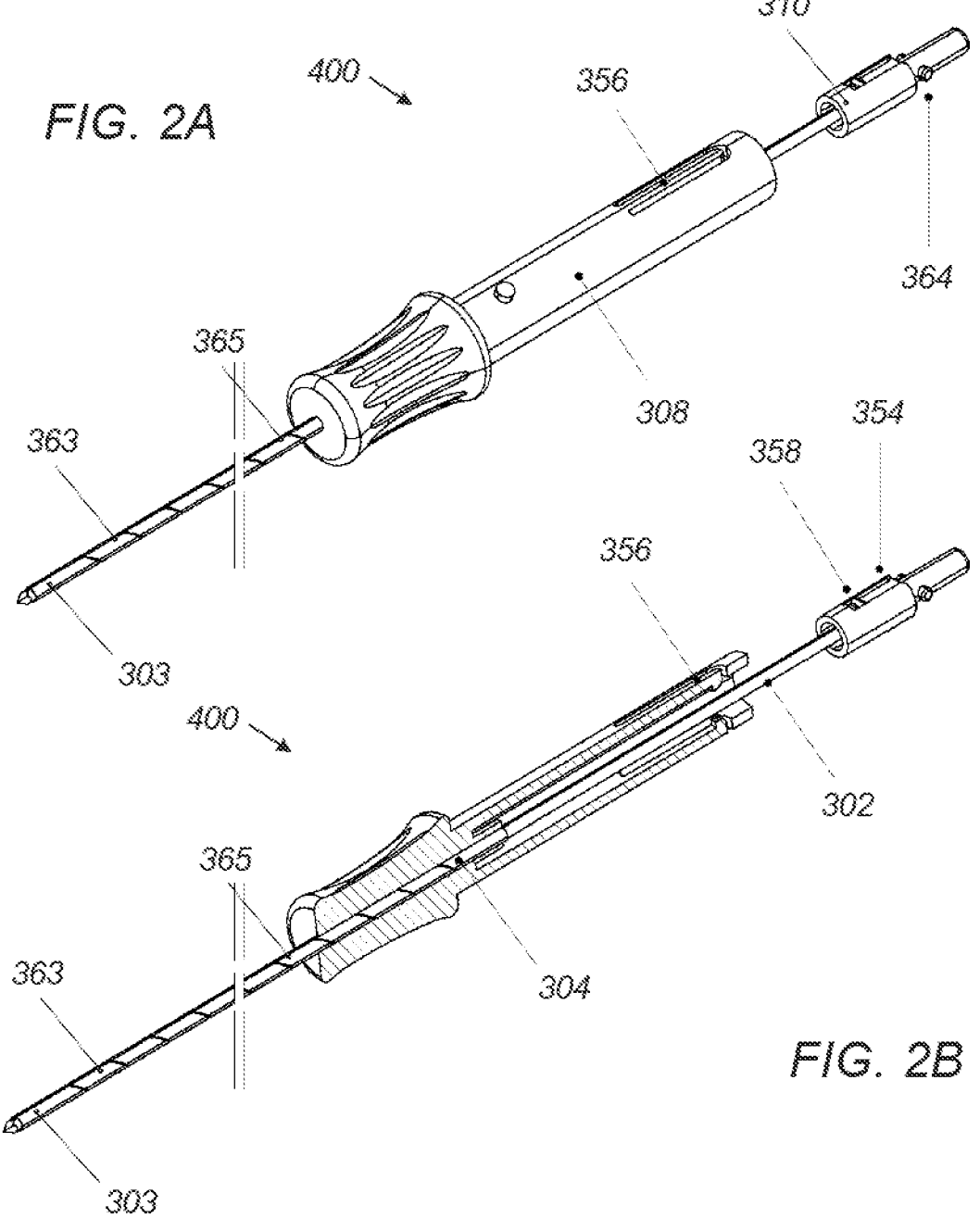
FIGS. 2A and 2B schematically illustrate a needle assembly, in accordance with some embodiments of the present disclosure.

According to some embodiments of the present disclosure, a stylet needle 302, coring needle 304, along with a cartridge 308 and a stylet lug 310 combine as needle assembly 400 (see FIGS. 2A and 2B). Catheter 376 is coupled to the gun 300 with a first locking mechanism comprising a swivel 374 and a bayonet 378. The swivel 374 is fixed to the proximal end of the catheter 376. The bayonet 378 comprises opposing extensions or forks 382 with shoulders 384 at the tips of the forks 382. Preferably, there are two opposing extensions or forks 382. Bayonet 378 is freely rotatable around swivel 374 fixed to the catheter 376.

According to some embodiments of the present disclosure, the gun 300 comprises a housing 312 formed by a housing left 312*a* and a housing right 312*b*. The housing 312 holds multiple components that make up an advancing mechanism and a firing mechanism, including a ratchet bolt

306, a pawl 316, a handle lever 318, a compression spring 320, a firing pin 322, a firing screw 324, a pawl release nut 326, and rotating release knob 328. The advancing mechanism and firing mechanism are described below in more detail in relation to FIG. 6. One or more self-tapping screws 330 hold the housing 312 together, and a larger self-tapping screw 332 passes through housing left 312*a*, handle lever 318 and housing right 312*b*. Preferably, there are three self-tapping screws 330 holding the housing 312 together. Optionally, the self-tapping screws 330 are 3 mm screws while the larger self-tapping screw 332 is a 3.5 mm screw. A person skilled in the art would appreciate that the self-tapping screws 330 and 332 can be of any size as long as they secure the housing 312 and handle lever 318 together.

According to some embodiments of the present disclosure, ratchet bolt 306 slides freely within a channel formed within housing 312 by closing housing left 312*a* and housing right 312*b*. Similarly, pawl 316 also slides within the channel formed within housing 312 by closing housing left 312*a* and housing right 312*b* and has a pawl locking tooth 346 that engages with the underside of ratchet bolt 306. Handle lever 318 rotates around a shaft split between housing left 312*a* and housing right 312*b*. The ratchet bolt 306 and the pawl 316 pass through and interact directly with handle lever 318. Compression spring 320 is located within the rear of the ratchet bolt 306 and housing 312. Firing pin 322 is aligned axially with the compression spring 320, the needle assembly 400 and the ratchet bolt 306. Firing screw 324 engages pawl release nut 326 internally and a firing pin 322 externally. Release knob 328 snaps onto the rear of the housing 312 and is axially aligned and keyed to the firing screw 324.

According to some embodiments of the present disclosure, housing 312 comprises a circular opening or socket 380. This circular opening or socket 380 accepts the forks 382 of bayonet 378. The forks 382 of bayonet 378 are compressed together during insertion then spring apart once inserted into the circular opening or socket 380. The shoulder 384 of each fork 382 catches against the inside of the housing 312, thus securing bayonet 378 to housing 312. Housing 312 further comprises facets 386 on housing left 312*a* and housing right 312*b* which allows closer alignment of gun 300 to the trajectory of catheter 376.

FIGS. 2A and 2B schematically illustrate a needle assembly 400, in accordance with embodiments of the present disclosure. Needle assembly 400 comprises a biopsy needle 363 made up of stylet needle 302 and coring needle 304, cartridge 308, and stylet lug 310. Biopsy needle 363 comprises a proximal end 365 and a distal end 303. Cartridge 308 and stylet lug 310 make up a second locking mechanism that locks the proximal end 365 of the biopsy needle 363 to the gun 300. In particular, cartridge 308 locks a proximal end of coring needle 304 to the gun 300, while stylet lug 310 locks a proximal end of stylet needle 302 to the cartridge 308 and gun 300. Coring needle 304 passes through a channel in cartridge 308 and is firmly adhered to cartridge 308, aligned by their common axis. Stylet needle 302 passes through coring needle 304 and is firmly adhered to stylet lug 310 which is located at the proximal end of the cartridge 308. Stylet lug 310 comprises channels 354 parallel to the direction of linear displacement. Preferably, there are two channels 354 and the two channels 354 are equi-spaced at 180 degrees apart. Each of the channels 354 include a raised cylindrical bump 358. The cartridge 308 comprises a plurality of longitudinal latch hooks 356 located within the proximal end of the cartridge 308, each of the longitudinal latch hooks 356 aligned with each of the channels 354 on stylet lug 310 and are prevented from sliding free by the raised cylindrical bumps 358. The latch hooks 356 also serve to lock the stylet lug 310 and stylet needle 302, preventing displacement relative to the cartridge 308 when the needle assembly 400 is inserted through the catheter 376.

FIGS. 3A, 3B and 3C schematically illustrate a needle assembly 400, a coring needle 304 of needle assembly 400 and stylet needle 302 of needle assembly 400 respectively in accordance with some embodiments of the present disclosure. Coring needle 304 is a thin-walled stainless steel tubing that slides freely over stylet needle 302. Stylet needle 302 may be a 16g needle with a sample collection indentation 360 at its distal end with a smaller cross-sectional area than the remainder of stylet needle 302. The coring needle 304 and stylet needle 302 together are too rigid to negotiate the curvature of, for example, the right brachiocephalic vein of a patient without puncturing the catheter 376 or damaging the distal tip of the one or both needles. To negotiate the tight curvature of the right brachiocephalic vein, stylet needle 302 and coring needle 304 must exhibit flexibility, which is determined by four variables. Maximum flexibility is afforded to the distal end of needle assembly 400 so as to protect the sample collection indentation 360 of the stylet needle 302.

According to some embodiments of the present disclosure, coring needle 304 is adapted to be more flexible by introducing a spiral cut to a length 'a' along its axial length, with a pitch length 'b' between each spiral. Preferably, the width of the spiral cut may between 0.01 to 0.3 mm and ideally 0.1 mm. The length 'a' can be any length extending along the coring needle 304. The spiral cut may be continuous or segmented along length 'a'. The person skilled in the art would appreciate that length 'a' need not extend fully to the cartridge 308. Preferably, the start of the spiral cut at the distal end of the coring needle 304 is located 2.5 mm away from a bevelled distal end of coring needle 304. The pitch length 'b' between each spiral may be of any length, and preferably 6 mm. The pitch length 'b' may be constant or may vary across the entire length 'a' of the spiral cut. Preferably, pitch length 'b' is 2 mm at the distal end of the coring needle 304, increasing to 4 mm at a middle portion of the coring needle 304 and increasing to 6 mm at the proximal end of the coring needle 304. The person skilled in the art would appreciate that the pitch 'b' of the coring needle 304 must be sufficiently small such that when the coring needle 304 is guided through the catheter 376 in the vicinity of the brachiocephalic vein, each spiral can adapt to the radius of the brachiocephalic vein without each individual spiral segment adopting a linear orientation. If the spiral segments adopt a linear orientation, the edge of each spiral would be misaligned and the relatively square corner of each edge could potentially abrade the inside of the catheter 376. A person skilled in the art would also appreciate that if the pitch 'b' is too small, the sum of all the gaps between each spiral would compress during firing, effectively reducing the penetration depth of the coring needle 304.

According to some embodiments of the present disclosure, stylet needle 302 is adapted to be more flexible by introducing notches to a length 'c' from its distal end with a pitch 'd' between notches. The length 'c' may be of any length extending along the stylet needle 302. The person skilled in the art would appreciate that length 'c' need not extend too proximately from the sample collection indentation 360 of the stylet needle 302. The pitch 'd' may be of any length. Preferably, the pitch 'd' of the notches may be between 0.5 to 5 mm and ideally 2 mm.

FIG. 3D schematically illustrates the bending of an unnotched stylet needle 302, while FIG. 3E schematically illustrates the bending of a notched stylet needle 302, in accordance with some embodiments of the present disclosure. Because the sample collection indentation 360 presents a smaller cross-sectional area than the remainder of the stylet needle 302, the proximal end 362 of the sample collection indentation 360, in relation to the free end that penetrates the target organ, is representative of the fixed end of a cantilever such that for any force applied to the free end of the stylet needle 302, the maximum bending moment, and stress concentration, will occur at said proximal end 362 of the sample collection indentation 360 due to the abrupt change of cross sectional area (see FIG. 3D). Thus, notches are introduced to the stylet needle 302 to reduce the tendency for the maximum bending moment in said stylet needle 302 to occur at the proximal end 362 of the sample collection indentation 360 (see FIG. 3E). Preferably, the notches are diametrically opposed pairs of notches rotated 90 degrees axially and spaced apart by pitch 'd' for a distance of 'c'. Preferably, the notches are approximately 0.1 mm in width, with a depth of not more than 30% of the diameter of stylet needle 302. The notches enable stylet needle 302 to adopt a progressive rate of change of curvature within the more flexible spiral cut coring needle 304 as both negotiate the catheter 376 as the forces of bending are effectively distributed along stylet needle 302 instead of being concentrated at the proximal end 302 of the sample collection indentation 360, with each notch itself becoming a stress concentrator. The person skilled in the art would thus appreciate that the length 'a' and pitch 'b' of coring needle 304 are tuned to stylet needle 302 for the various gauges.

Figures 4, 5A:
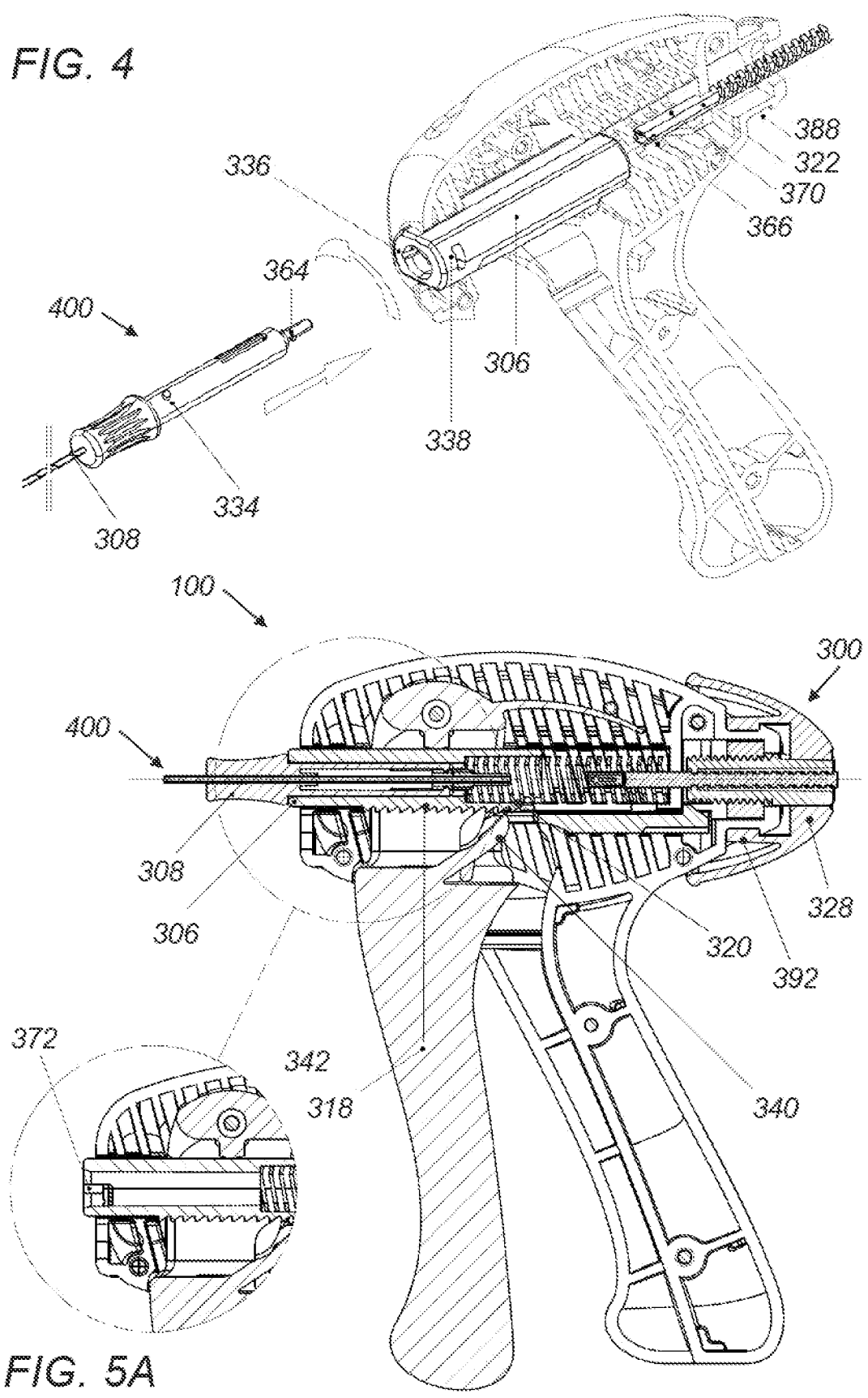
FIG. 4 schematically illustrates a mechanism by which a needle assembly locks onto a gun, in accordance with some embodiments of the present disclosure.
FIGS. 5A to 5D schematically illustrate cross-sections of a biopsy device showing the process of locking and loading a needle assembly onto a gun, in accordance with some embodiments of the present disclosure.

FIG. 4 schematically illustrates the mechanism by which needle assembly 400 locks onto gun 300, in accordance with some embodiments of the present disclosure. Cartridge 308 of needle assembly 400 comprises a plurality of cartridge pegs 334. Preferably, there are two cartridge pegs 334 that are diametrically opposite to each other. Ratchet bolt 306 of gun 300 comprises alignment slots 336. The cartridge pegs 334 are aligned with alignment slots 336 in the ratchet bolt 306. The needle assembly 400 is locked onto the gun 300 through linear displacement followed by rotational displacement, as illustrated by the arrows. Preferably, the rotational displacement may be between 60 to 70 degrees, and ideally 65 degrees. Rachet bolt 306 of gun 300 further comprises raised projections 338 in the circular portion of the alignment slots 336 to effectively narrow the width of said alignment slots 336 and offer tactile feedback to confirm that needle assembly 400 is secured onto gun 300. Preferably, there are two raised projections 338. Once the needle assembly 400 is inserted into gun 300 and twisted, the needle assembly 400 is locked into position and cartridge 308 will be displaced together in unison with the ratchet bolt 306. At this point in time, stylet lug 310 has not yet engaged with firing pin 322.

Figure 5B:
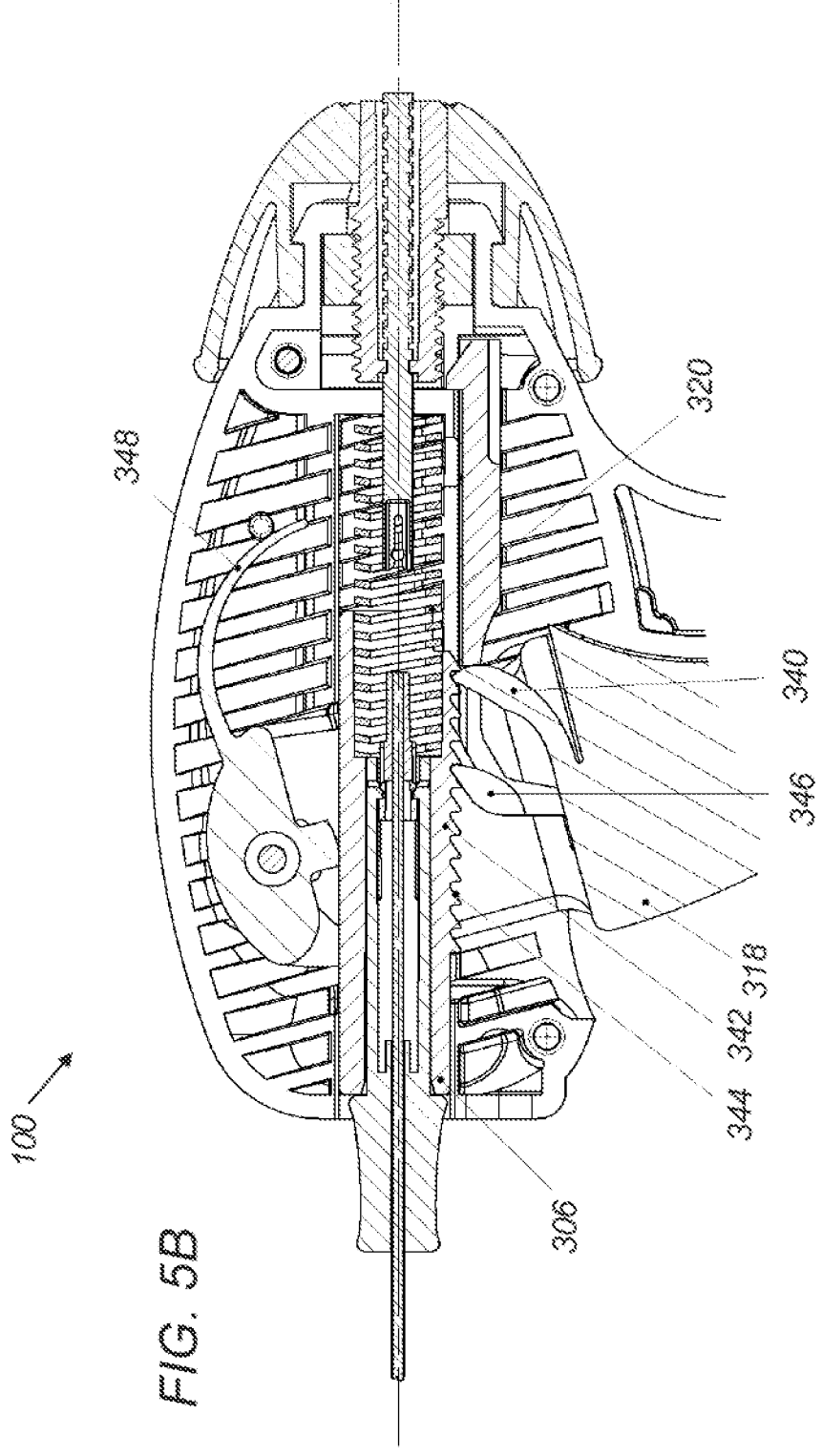
Figure 5C:
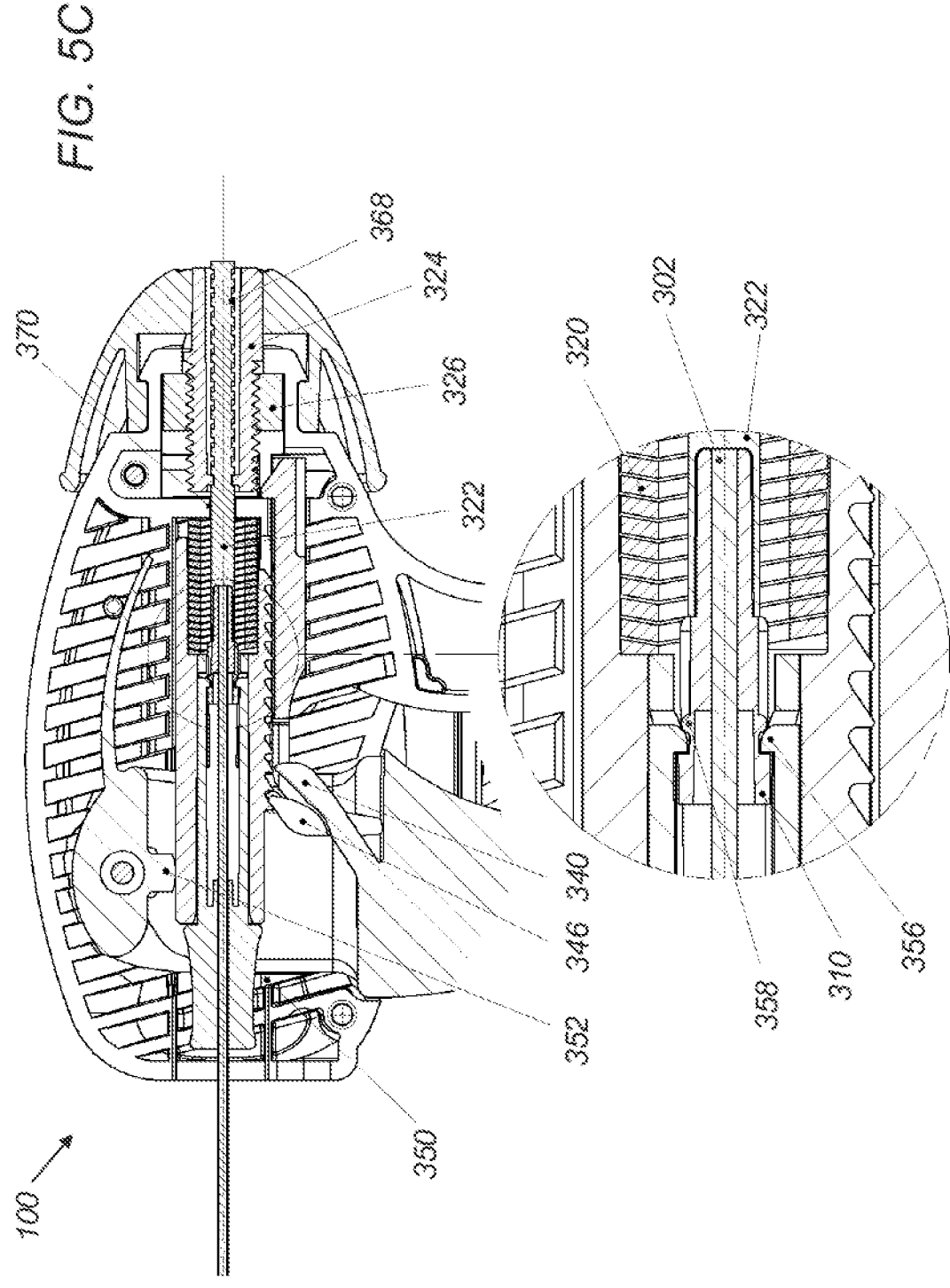

FIGS. 5A to 5D schematically illustrate cross-sections of a biopsy device 100 showing the process of locking and loading a needle assembly 400 onto gun 300, in accordance with some embodiments of the present disclosure. FIG. 5A illustrates gun 300 with needle assembly 400 inserted, ready to commence lever action by handle lever 318. FIG. 5B illustrates gun 300 with needle assembly 400 inserted, with handle lever 318 fully rotated. FIG. 5C illustrates gun 300 with needle assembly 400 inserted, with ratchet bolt 306 preloading compression spring 320 and stylet lug 310 retained by longitudinal latch hooks 356 of cartridge 308.

Figure 5D:
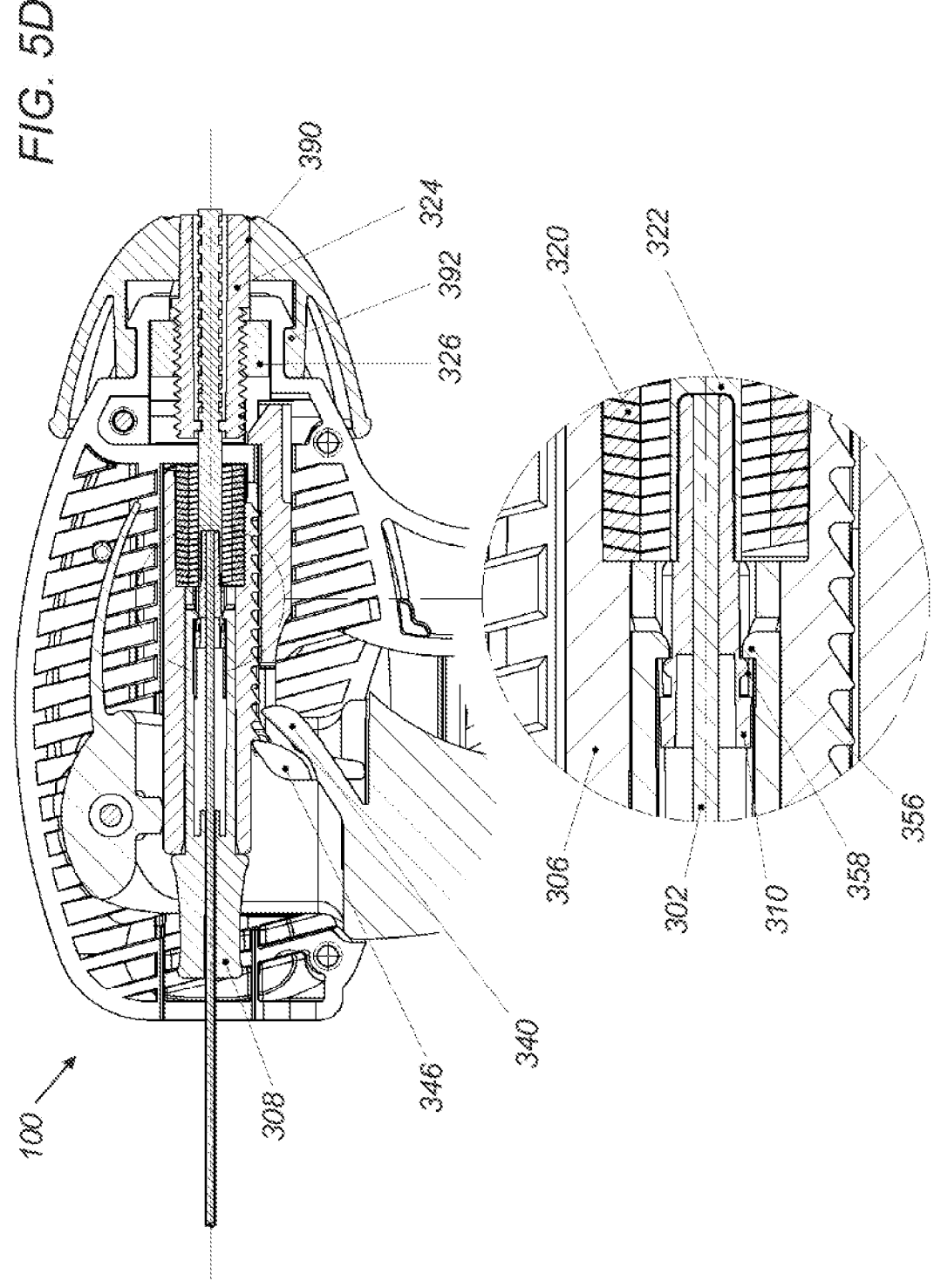

FIG. 5D illustrates gun 300 with needle assembly 400 inserted, with stylet lug 310 released from longitudinal latch hooks 356 of cartridge 308.

According to some embodiments of the present disclosure, ratchet bolt 306 comprises a gear rack 342 with multiple teeth. The gear rack 342 with multiple teeth is part of the ratchet bolt 306 and determines the extent of linear displacement of ratchet bolt 306. Handle lever 318 comprises a flexible finger 340. The flexible finger 340 of handle lever 318 engages the gear rack 342. Handle lever 318 may rotate anti-clockwise when it is squeezed. Preferably, handle lever 318 rotates through a maximum arc of 15 degrees. Each squeezing or rotating action of the handle lever 318 produces a linear displacement of the ratchet bolt 306 which pre-loads compression spring 320 of gun 300. Preferably, the linear displacement of the ratchet bolt 306 is equal to at least one pitch of the gear rack 342 and a maximum of two pitches of the gear rack 342. The total sum of linear displacements, or pre-load applied to compression spring 320, is equal to the firing stroke of coring needle 304. Optionally, the stroke is 30 mm. A person skilled in the art would appreciate that the stroke length can be increased or decreased by the number of teeth in the gear rack 342 and the corresponding length of the ratchet bolt 306. With each handle lever 318 rotation action and subsequent linear displacement of the ratchet bolt 306, the relief angle 344 afforded to each tooth on the ratchet bolt 306 deflects the pawl locking tooth 346 on the pawl 316 sufficiently so that said pawl locking tooth 346 is denied engagement with the ratchet bolt 306. Upon release of the handle lever 318, a cantilever spring 348 integral with the handle lever 318 returns the handle lever 318 to its original position ready to repeat the lever action. At this same time, the pawl locking tooth 346 on the pawl 316 instantly re-engages the ratchet bolt 306, maintaining pre-load on the compression spring 320. Although FIGS. 5A and 5B illustrate the ratchet bolt 306 as a simply supported beam i.e. it is constrained at both ends by the channel in the housing 312a and 312b, within which it slides, a person skilled in the art would appreciate that with continued linear displacement of the ratchet bolt 306, the ratchet bolt 306 becomes disengaged from the housing distal end 350 (see FIG. 5C) presenting itself as a cantilever when engaged by the rotational inertia of a flexible finger 340 on the handle lever 318. Therefore, to constrain this rotational degree of freedom, a fulcrum 352 on the cantilever spring 348 offers a tangential radial sweep that maintains a sufficient point of contact against the ratchet bolt 306, resisting any rotational moment of inertia.

According to some embodiments of the present disclosure, stylet lug 310 further comprises small stylet lug pegs 364 and firing pin 322 further comprises keyhole slots 366. Preferably, there are two small stylet pegs 364. As the ratchet bolt 306 approaches full pre-load displacement, the small stylet lug pegs 364 on the stylet lug 310 are aligned with keyhole slots 366 in firing pin 322. When the total displacement of ratchet bolt 306 and the cartridge 308 is within 2 mm of full pre-load, stylet lug 310 is completely engaged with firing pin 322 (see FIG. 5C.)

According to some embodiments of the present disclosure, firing pin 322 comprises a dual start square thread 368 and two opposed flats 370 along its length. The firing pin 322 cannot offer any linear displacement until the firing screw 324 is rotated as the two opposed flats 370 along its length prevent it from rotating within the squared alignment slot 372 in the housing 212. During the final handle lever 318 action (see FIG. 5B) and linear displacement of the ratchet bolt 306, the firing pin 322 bumps the stylet lug 310 clear of the latch hooks 356 in the ratchet bolt 306. Comparing the enlarged view in FIG. 5D to FIG. 5C shows said latch hooks 356 now proximal to the raised cylindrical bump 358. Once the needle assembly 400 is locked onto gun 300 and loaded, the operator may now connect the catheter 376 to the gun 300.

Figure 6:
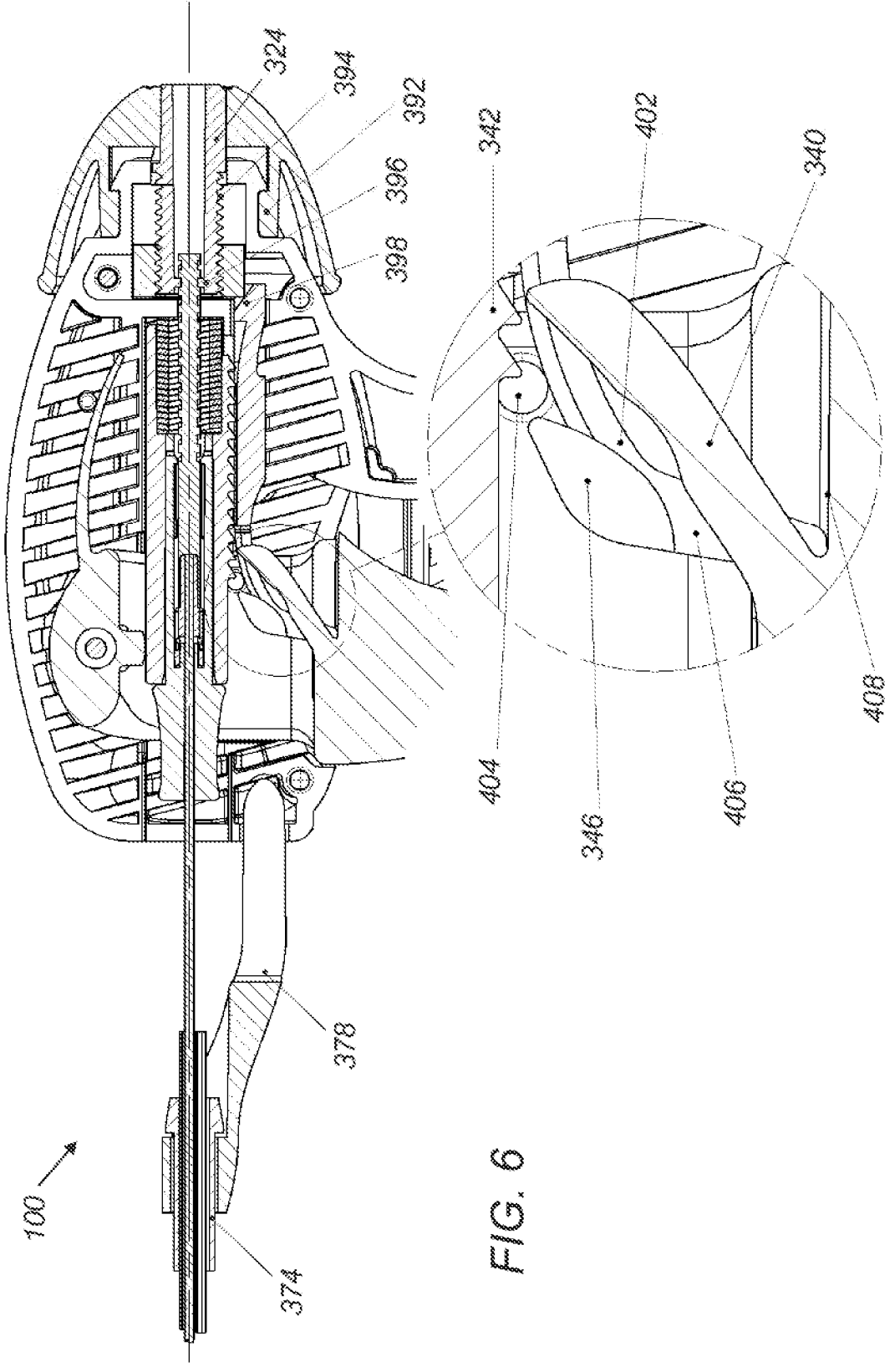
FIG. 6 schematically illustrates a cross-section of a biopsy device with a needle assembly and a catheter connected to a gun before firing, in accordance with some embodiments of the present disclosure.

FIG. 6 schematically illustrates a biopsy device 100 with a needle assembly 400 and a catheter 376 connected to gun 300 before firing with compression spring 320 fully pre-loaded and pawl 316 fully deformed, in accordance with some embodiments of the present disclosure. After the catheter 376 is connected to housing 312, the operator advances stylet needle 302 into the target organ through rotating an advancing mechanism as detailed below. Advancing mechanism may be a release knob 328, which is a rotatable advancing mechanism. Other advancing mechanisms may also be employed. Since advancing stylet needle 302 would cause catheter 376 to move, bayonet 378 negates any equal and opposite reaction force created by the advancement and penetration of stylet needle 302 into the tissue of the patient. This is because catheter 376 is coupled to the gun 300 with bayonet 378, independent of stylet needle 302 and coring needle 304. Direct coupling of catheter 376 to gun 300 with bayonet 378 also confers multiple advantages, including stabilizing the proximal end of catheter 376 and allowing the operator to advance stylet needle 302 without holding onto catheter 376.

According to some embodiments of the present disclosure, release knob 328 rotates within a peripheral channel 388 in the assembled housing 312 (see FIG. 1B). During assembly, said release knob 328 is aligned with a plurality of flats 390 (see FIGS. 1B and 5D) on the shaft of the firing screw 324. Preferably, there are three flats 390. As release knob 328 is being pushed onto housing 312, one or more snap-on claws 392 with undercut interfere with the outer perimeter of the peripheral channel 388. Preferably, there are four snap-on claws 392. Application of moderate force deflects snap-on claws 392, allowing release knob 328 to align to slide further along the firing screw 324. The undercut of each snap-on claw 392 snaps or recovers static position, aligned within the peripheral channel 388. The firing screw 324 can now only rotate together with the release knob 328. The firing screw 324 has an external left hand thread 394. The internal diameter offers clearance to the firing screw 324 but has keys 396 raised from the internal diameter that engage the dual start square thread 368 of the firing screw 324. Preferably, there are two keys 396. Clockwise rotation of the release knob 328 causes the firing screw 324 to advance the firing pin 322, stylet lug 310 and the stylet needle 302 into the target organ. Preferably, one complete clockwise rotation of the release knob 328 causes the firing screw 324 to advance the firing pin 322, stylet lug 310 and the stylet needle 302 into the target organ by 6 mm; whilst the pawl release nut 326 is displaced by 1.75 mm; an amount equal to the pitch of the external left hand thread 394 of the firing screw 324.

According to some embodiments of the present disclosure, the two linear displacements will proceed in unison as the release knob 328 is rotated clockwise through, for example, five complete rotations to advance the firing pin 322, stylet lug 310 and the stylet needle 302. During the final rotation, the pawl release nut 326 continues to apply a compressive force against an angled heel 398 of the pawl 316. The angled heel 398 is essentially a small cantilever whose length and thickness are tuned according to the polymer from which it is moulded, so that it will deform and be displaced linearly. This linear displacement forces the neck of the pawl 402 against raised circular stops 404 on the handle lever 318; one either side of said handle lever 318 straddling the ratchet bolt 306. These raised circular stops 404 serve two purposes, firstly the handle lever 318 is fully returned ensuring the flexible finger 340 is clear of the ratchet bolt 306. Secondly, the neck of the pawl 402 is further compressed against said raised circular stops 404 and the horns of the pawl 406 firmly contact the clearance channel 408 in the handle lever 318. The neck of the pawl 402 is now a simply supported beam; maximum deflection occurs in the centre of the beam i.e., the pawl locking tooth 346 plastically deforms clear of the gear rack 342 on the ratchet bolt 306. The stylet needle 302 is now fully advanced by the advancing mechanism of gun 300.

According to some embodiments of the present disclosure, the operator operates a firing mechanism and fires ratchet bolt 306 by pressing the handle lever 318 after the final rotation of the release knob 328. Pressing handle lever 318 causes pawl locking tooth 346 to disengage gear rack 342, causing all the preload on the compression spring 320 to release and thus fire the ratchet bolt 306. As the ratchet bolt 306 is fired, the cartridge 308 and coring needle 304 coupled to the ratchet bolt 306 are fired into the target organ of the patient, thus collecting a sample within the sample collection indentation 360.

Figure 7:
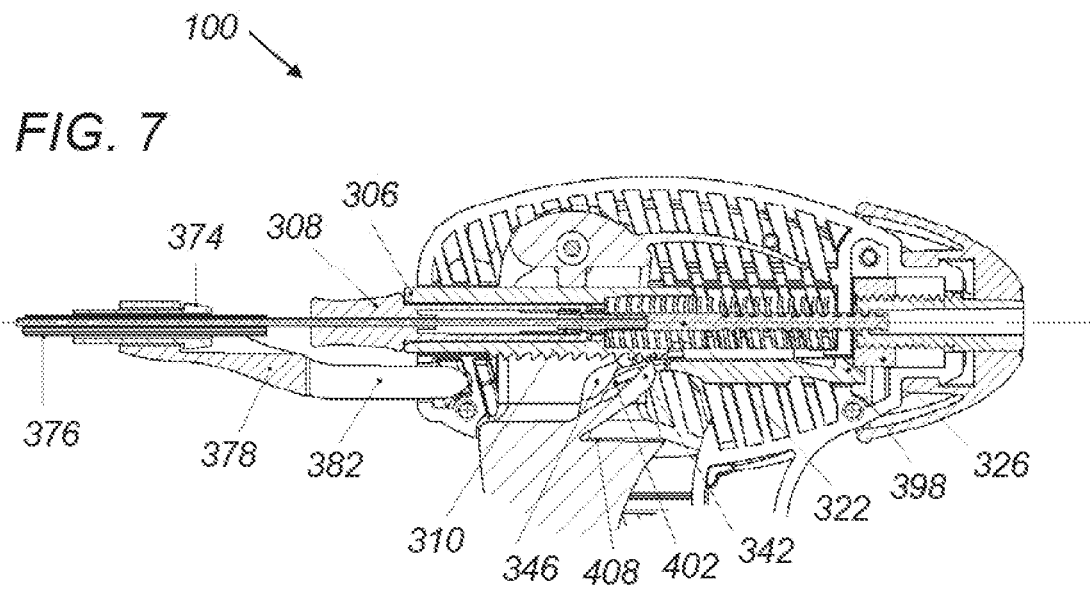
FIG. 7 schematically illustrates a cross-section of a biopsy device with a needle assembly and a catheter connected to a gun after firing, in accordance with some embodiments of the present disclosure.

FIG. 7 schematically illustrates a cross-section of a biopsy device 100 with a needle assembly 400 and a catheter 376 connected to gun 300 after firing, in accordance with some embodiments of the present disclosure. During firing of ratchet bolt 306, stylet needle 302 is constrained by virtue of the small stylet lug pegs 364 on the stylet lug 310 gripped by the keyhole slots 366 on the firing pin 322. The coring needle 304 has entered the target organ, shaved and trapped the tissue sample in the space between the sample collection indentation 360 and the inside of said coring needle 304.

Figure 8:
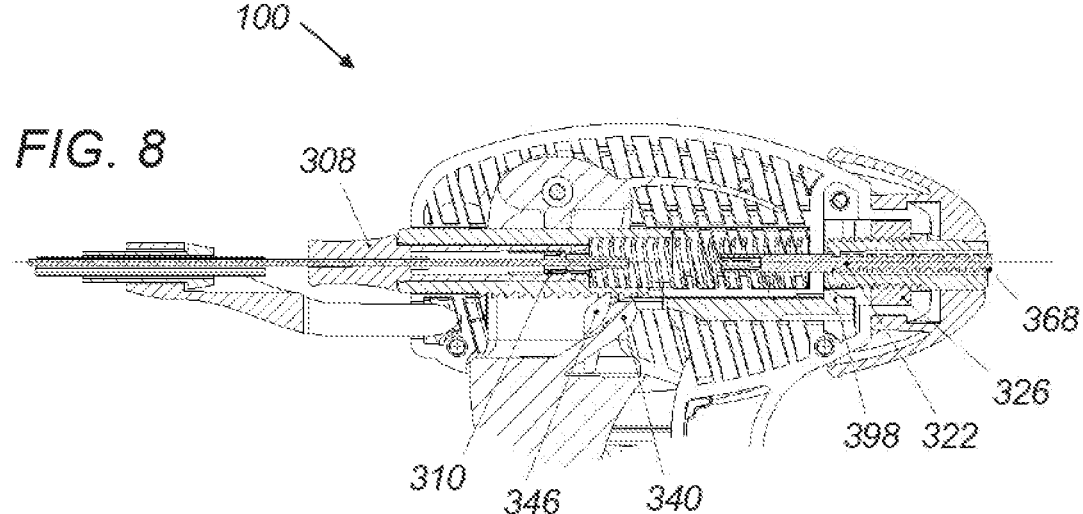
FIG. 8 schematically illustrates a cross-section of a biopsy device with a needle assembly and a catheter connected to a gun with firing pin retracted, in accordance with some embodiments of the present disclosure.

FIG. 8 schematically illustrates a cross-section of a biopsy device 100 with a needle assembly 400 and a catheter 376 connected to gun 300 with firing pin 322 retracted, in accordance with some embodiments of the present disclosure. After firing, release knob 328 must be rotated anti-clockwise until it is unable to be rotated. This can be confirmed by the appearance of the proximal end of the firing pin 322 protruding from the firing screw 324 as shown in FIG. 8. The firing pin 322 has released the stylet lug 310. The needle assembly 400 can now rotated and withdrawn from the gun 300 which is now ready to accept another set of needle assembly 400.

Methods for performing a biopsy using biopsy device 100 comprising gun 300, needle assembly 400 and catheter 376 are described herein below in accordance with some embodiments of the present disclosure. An operator, such as a doctor, may insert catheter 376 with swivel 374 and bayonet 378 connected into a first blood vessel of the patient. The operator navigates the distal end 375 of catheter 376 though the vascular system to a second blood vessel near the biopsy site of the target organ. Once catheter 376 is secured within the second blood vessel at the target organ, needle assembly 400 is inserted through the catheter 376 to a depth whereby the distal end of stylet needle 302 is near to but not yet penetrating the target organ. The operator may then introduce the gun 300 to the proximal end 365 of the biopsy needle. The operator may couple the gun 300 to needle assembly 400 by fully inserting needle assembly 400 into handle 300 and locking the needle assembly 400 into gun 300 by rotating the needle assembly 400 anti-clockwise (see FIG. 4).

The operator may squeeze and release the handle lever 318 of the gun 300 several times until the handle lever 318 can no longer be squeezed as stylet lug 310 has been released from longitudinal latch hooks 356 of cartridge 308 (see FIGS. 5A to 5D). This indicates that the firing mechanism of the gun 300 is fully loaded and ready to fire. The gun 300 should now be aligned to the trajectory of the needle assembly 400. The facets 386 on either side of the gun housing 212 may allow closer alignment against the patient's arm. At this juncture, the operator may attach the catheter 376 to the gun 300 (see FIG. 6) The operator may snap-lock the bayonet 378 that swivels around the proximal end of the catheter 376 into the gun 300. This ensures that the gun 300 maintains a fixed relationship to the catheter 376 when stylet needle 302 is advanced and coring needle 304 is fired by stabilizing the proximal end of catheter 376 and coupling catheter 376 directly to gun 300

The inter-relationship of the needle assembly 400 and the catheter 376 should have positioned stylet needle 302 against the target organ or at most slightly penetrating the target organ. The operator may then rotate the release knob 328 on the rear of gun 300 clockwise to advance needle stylet 302 into the target organ, with one full rotation advancing the stylet needle 302 by 6 mm. After 5 full rotations and during the sixth rotation, stylet needle 302 is fully advanced and the ratchet bolt 306 is ready fire. When the operator squeezes handle lever 318 after stylet needle 302 is fully advanced, coring needle 304 is released by the ratchet bolt 306 and fires into the target organ (see FIG. 7). At any time prior to this release, the needle stylet 302 can be retracted and repositioned. After firing, the operator may retract the release knob 328 by rotating the release knob 328 anti-clockwise until it is unable to be rotated anymore (see FIG. 8). This releases the internal firing mechanism from the needle assembly 400. Thereafter, the needle assembly 400 can be rotated clockwise and removed. The gun 300 is ready to receive another set of needles should additional biopsy samples be required.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A biopsy device for acquiring a biopsy sample of a target organ in a subject, the biopsy device comprising:
   a housing;
   an elongated tube with a first proximal end and a first distal end, wherein the first distal end is positioned at a biopsy site of the target organ, and wherein the first proximal end comprises a first locking mechanism having a swivel disposed around the elongated tube and a bayonet externally coupled to the swivel, said bayonet attached to an external portion of the housing; and a biopsy needle with a second proximal end and a second distal end, the biopsy needle is positioned within the elongated tube for navigation to the biopsy site and is configured to exit the first distal end of the elongated tube for penetration into tissue of the target organ at the biopsy site, and to acquire a biopsy sample of the target organ at the biopsy site, wherein the second proximal end of the biopsy needle having a second locking mechanism comprising a cartridge and a stylet lug disposed around the biopsy needle, the cartridge and the stylet lug each coupled to and enclosed within the housing.

2. The biopsy device according to claim 1, wherein the first locking mechanism comprises opposing extensions configured to engage with an opening in the housing.

3. The biopsy device according to claim 2, wherein each of the opposing extensions comprise a shoulder configured to engage with the opening in the housing.

4. The biopsy device according to claim 1, wherein the first locking mechanism is freely rotatable around the elongated tube.

5. The biopsy device according to claim 1, wherein the biopsy needle comprises a coring needle and a stylet needle.

6. The biopsy device according to claim 5, wherein the coring needle comprises one or more spiral cuts extending circumferentially around and longitudinally along the coring needle.

7. The biopsy device according to claim 6, wherein the one or more spiral cuts has a constant pitch.

8. The biopsy device according to claim 6, wherein the one or more spiral cuts has a variable pitch.

9. The biopsy device according to claim 5, wherein the stylet needle comprises notches along its circumference longitudinally along the stylet needle.

10. The biopsy device according to claim 9, wherein the notches are diametrically opposed.

11. The biopsy device according to claim 9, wherein the notches are of a depth of not more than 30% of the stylet needle diameter.

12. The biopsy device according to claim 9, wherein the notches are rotated 90 degrees axially.

13. The biopsy device according to claim 5, wherein the housing further comprises:

an advancing mechanism, configured to advance the stylet needle for penetration into tissue of the target organ at the biopsy site; and a firing mechanism, configured to fire the coring needle for penetration into tissue of the target organ at the biopsy site, thereby obtaining the biopsy sample of the target organ at the biopsy site.

14. The biopsy device according to claim 13, wherein the advancing mechanism is actuated by rotation.

15. The biopsy device according to claim 13, wherein the firing mechanism is configured to fire the coring needle only when the stylet needle is fully advanced.

16. The biopsy device according to claim 5, wherein the stylet needle comprises an indentation at a third distal end of the stylet needle.

17. A method for acquiring a biopsy sample of a target organ in a subject using a biopsy device, the method including:

providing a biopsy device, the biopsy device comprising:

a housing;

an elongated tube with a first proximal end and a first distal end, wherein the first distal end is positioned at a biopsy site of the target organ, and wherein the first proximal end comprises a first locking mechanism having a swivel disposed around the elongated tube and a bayonet externally coupled to the swivel, said bayonet attached to an external portion of the housing; and a biopsy needle with a second proximal end and a second distal end, the biopsy needle is positioned within the elongated tube for navigation to the biopsy site and is configured to exit the first distal end of the elongated tube for penetration into tissue of the target organ at the biopsy site, and to acquire a biopsy sample of the target organ at the biopsy site, and wherein the second proximal end of the biopsy needle comprises a second locking mechanism, said second locking mechanism comprising a cartridge and a stylet lug disposed around the biopsy needle, the cartridge and the stylet lug each coupled to and enclosed within the housing wherein the second proximal end of the biopsy needle having a second locking mechanism comprising a cartridge and a stylet lug disposed around the biopsy needle, the cartridge and the stylet lug each coupled to and enclosed within the housing;

percutaneously inserting the elongated tube into a first blood vessel of a limb of a subject; and navigating the first distal end of the elongated tube from the first blood vessel through a vascular system of the subject and into a second blood vessel of the target organ near the biopsy site.

18. The method according to claim 17, wherein the first locking mechanism comprises opposing extensions configured to engage with an opening in the housing.

19. The method according to claim 18, wherein coupling the elongated tube to the housing with the first locking mechanism comprises:

compressing the opposing extensions; and inserting the compressed opposing extensions into the opening in the housing.

20. The method according to claim 17, wherein the biopsy needle comprises a coring needle and a stylet needle.

21. The method according to claim 20, further comprising:

pushing the stylet needle into the target organ at the biopsy site until the stylet needle is fully advanced; and pushing the coring needle into the target organ at the biopsy site.

* * * * *